June 18, 1946. H. C. SWIM Plant Pat. 698
HIBISCUS PLANT
Filed Aug. 27, 1945
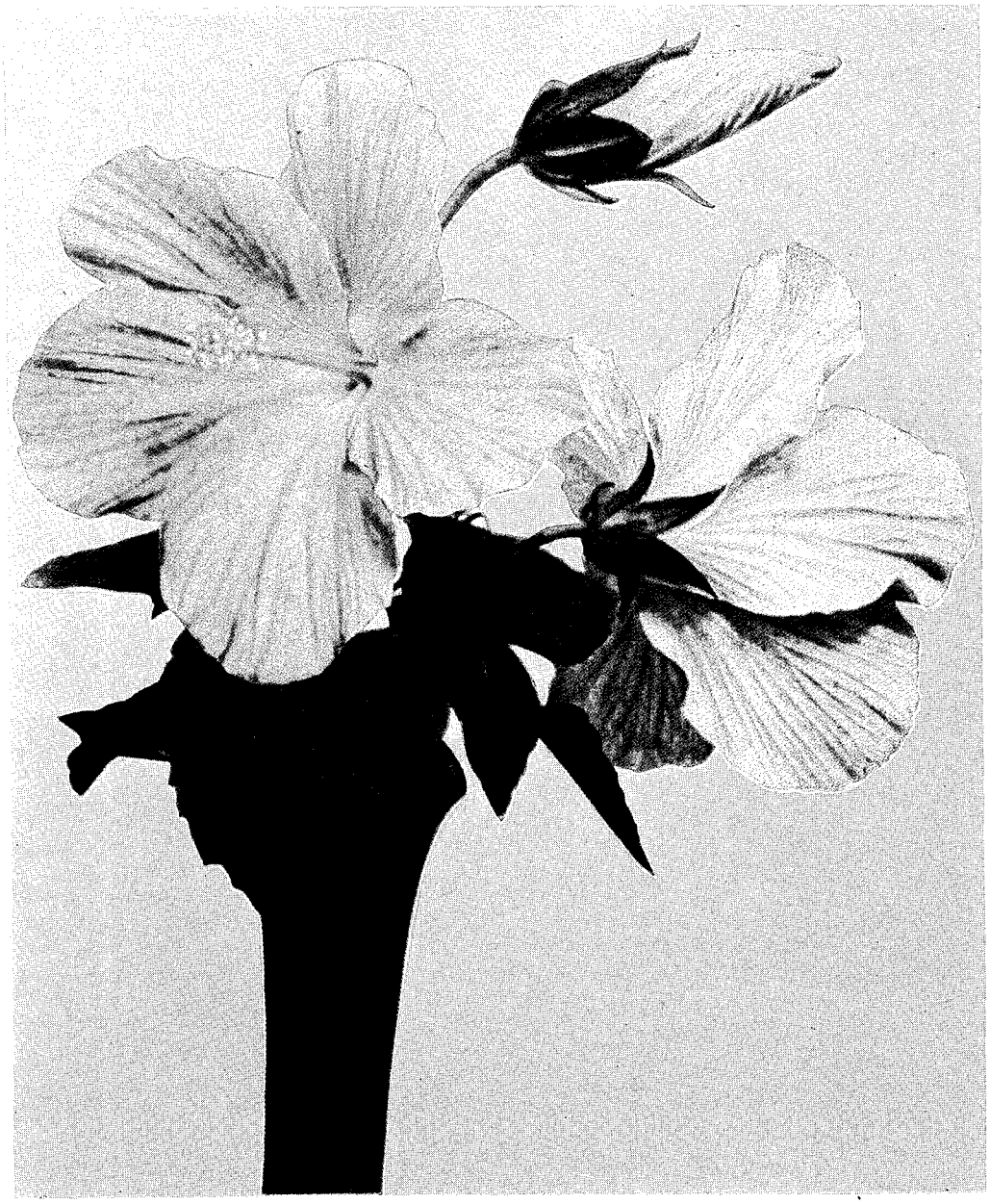
Inventor
H. C. Swim
By Robb & Robb
His Attorneys Patented June 18, 1946

Plant Pat. 698

UNITED STATES PATENT OFFICE

698

HIBISCUS PLANT

Herbert C. Swim, Ontario, Calif., assignor to Armstrong Nurseries, Inc., Ontario, Calif., a corporation of California Application August 27, 1945, Serial No. 612,839

1 Claim. (Cl. 47—60)

The present discovery relates to a new and distinct variety of hibiscus plant, of the Hibiscus-Rosa-sinensis class, discovered and selected by me from a group of seedlings originating from a cross of two unnamed varieties, one a frilled deep yellow with maroon eye or throat, and the other a large deep yellow with light eye or throat.

This new variety differs substantially not only from both of its parents, but from all other varieties in commerce known to me, particularly in respect to the combination of color in the flower, as specifically set forth hereinafter.

The drawing shows specimens of the present variety in various stages of development.

The present variety is further characterized as to novelty by the showy floriferousness of the plants, their ability to begin flowering while still very young, the large size of the flowers and slight modification of the tendency of most varieties of this species to have extremely abrupt reflexed petals in the early stage of bloom.

Other notable features of novelty of this variety are found in its free branching habit and in the characteristics of the foliage—large, dark green, glossy, flat, heart-shaped and crenate leaves.

I have asexually reproduced the variety by cuttings and have found the foregoing characteristics to be established and to come true to form in the progeny.

The following is a detailed description of the new variety, all references to color being in accordance with the R. F. Wilson's Horticultural Colour Chart, except where indicated to be in accordance with Ridgway's Color Standards and Nomenclature:

*Plant*

Type: Tender—shrub.

Class: Hybrid, variety of Hibiscus Rosa-sinensis.

Seedling:

*Seed parent.*—Unnamed seedling having a flower of frilled deep yellow with maroon eye or throat.

*Pollen parent.*—Unnamed seedling having a flower of large deep yellow with light eye or throat.

Propagation: By cuttings, the only method tried so far.

Leaves: Usually cordate, sometimes ovate.

*Margins.*—Crenate. Teeth of rounded outline, short sharp point to teeth. Main veins arranged palmately with capillary veins originating alternately and becoming anastomose. *Length of leaves*—usually 4¼ to 4½" long, 3½ to 4" wide at widest part of leaf, sometimes larger. *Color*—dark dull yellow green, Plate XXXII (Ridgway), veined with deep dull yellow green (1), Plate XXXII (Ridgway). New leaves deep dull yellow green (1), veined with same color, Plate XXXII (Ridgway). Stems—Parrot Green, Plate VI (Ridgway), on older leaves Cedar Green, Plate VI (Ridgway). Under side of leaves—deep dull Yellow Green (1), Plate XXXII (Ridgway). Under side of newer leaves—Chromium Green, Plate XXXII (Ridgway). New leaves—near Parrot Green, Plate VI (Ridgway); under side same.

*Petiole.*—1½ to 2" long, with many inconspicuous lenticels, otherwise smooth; at about 90° angle with stem. Medium to short in length and medium stout.

*Stipules.*—¼ to ½" long, usually thin, later deciduous; usually pointed at about a 45° angle with stem, sometimes more.

*Flower*

Flower described grown under glass in month of December at night minimum temperature of 60° F. and maximum daytime temperature of 85° F.

*Petals.*—3¾ to 4 inches long, overlapping for ¾ or more of their length.

*Diameter.*—6½ to 7 inches. Single with five petals.

*Stamen tube.*—5 inches long, ¼ inch in diameter at base to $\frac{5}{32}$ inch in diameter at point of attachment of lowest anther. *Color*—Marigold Orange, Plate 11/1, page 11, at base, gradually changing to near Geranium Lake, Plate 20/2, page 20. Filaments from near Fire Red, Plate 15/2, page 15, at base, to near Geranium Lake, Plate 20/2, page 20, at tip. Stamens sparse near base increasing in proximity to one another at tip; 70–80 in number.

*Stigma.* — Five-parted. *Color* — between Dutch Vermilion, Plate 717, page 156, and Signal Red, Plate 719, page 93.

*Style.*—Inside—covered thickly with straight stiff hairs approximately $\frac{1}{32}$ inch long. Color—near Signal Red, Plate 719/2, page 93. Outside—covered sparsely with short hairs of uneven length. Styles from point of emergence from stamen tube to point of divergence ¼ inch in length. Color—near White. Divided portions faintly tinted with Signal Red, Plate 719/3, page 93.

*Pollen.*—Near Indian Yellow, Plate 6/1, page 6.

*Shape of flower.*—Dish-shaped with throat narrow—petals to point emerging from calyx on an angle of approximately 80° from pedicel-sepal axis, thereafter curving gradually outward to a parallel position at point of overlapping and from this latter point reflexed more or less abruptly depending on age of flower. The angle of this reflex varies in inverse proportion to the age of the flower but does not vary to the extreme as such well known varities as "Prince Takamatsu." The petals overlap clockwise as viewed from inside flower, and each is ruffled and waved at a point between one inch and two inches from base on inside, and from end of sepals to slightly beyond point of overlapment on the outside. Petal 2¾ inches wide at broadest point (at end of overlap). Right margin more or less straight in outline from ½ inch of base to end of overlap. Apex rounded. Left margin curving much like a sickle.

*Color of flower.*—Inside of flower—In throat, near Saffron Yellow, Plate 7/1, page 7, gradually suffusing in center of petal and more abruptly at inner margin with near Fire Red, Plate 15/1, page 15, gradually becoming lighter beyond a point midway between base and apex to near a ground color of Saturn Red, Plate 13/2, page 13, which is overlaid with a color near Poppy Red, Plate 16/1, page 16, bordering netted veins (lateraling from main or larger veins, gradually diverging from base in the same way petal broadens from base to end of overlap). That part of the inside of the petal covered by the petal counterclockwise from it is mottled near Fire Red, Plate 15/2, page 15, on a ground color of Canary Yellow, Plate 2/3, page 2. Outside of flower—Color: Left half of each petal with ground color Empire Yellow, Plate 603/2, page 66, to Straw Yellow, Plate 604/2, page 67, predominant but mottled or dotted (increasingly toward middle) with near Nasturtium Red, Plate 14/3, page 14. Veins at tips Empire Yellow, Plate 603/3, page 66. Right half of petal near Nasturtium Red, Plate 14/2, page 14, except at base where there is a small area of Cadmium Orange, Plate 8/2, page 8.

*Peduncle.*—2 to 3 inches long, nearly glabrous with few long wool-like hairs and numerous inconspicuous lenticels which give a sensation to the touch such as would fine sandpaper. Pedicel ¼ to 1 inch long covered with long wool-like hairs. About 45° angle with stem before and after full development of flower; emerges at axis of leaf and stem.

Growth: Habit—free branching.

I claim:

A new and distinct variety of hibiscus plant, characterized as to novelty by color combination of its flowers; by the floriferousness of the plants and their ability to begin flowering while still very young; the large size of the flowers and form of petals in the early stage of bloom; the free branching habit of growth, and the size, form, color, texture and shape of leaves, substantially as shown and described.

HERBERT C. SWIM.